US010829648B2

(12) United States Patent
Polson et al.

(10) Patent No.: US 10,829,648 B2
(45) Date of Patent: *Nov. 10, 2020

(54) SUCCINATE DEHYDROGENASE INHIBITOR CONTAINING COMPOSITIONS

(71) Applicant: ARCH WOOD PROTECTION, INC, Atlanta, GA (US)

(72) Inventors: George Polson, Jasper, GA (US); Alex Valcke, Dessel (BE); Andrew Hughes, Pontefract (GB); Jody Jourden, Atlanta, GA (US); Maria Regina Prioli, Alpharetta, GA (US); Qi Zheng, Cumming, GA (US)

(73) Assignee: ARCH WOOD PROTECTION, INC., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/394,020

(22) Filed: Dec. 29, 2016

(65) Prior Publication Data

US 2017/0107380 A1 Apr. 20, 2017

Related U.S. Application Data

(63) Continuation of application No. 14/442,507, filed as application No. PCT/US2013/070777 on Nov. 19, 2013, now abandoned.

(60) Provisional application No. 61/728,062, filed on Nov. 19, 2012.

(51) Int. Cl.
| | | |
|---|---|---|
| A01N 43/56 | (2006.01) |
| A01N 33/00 | (2006.01) |
| A01N 43/40 | (2006.01) |
| A01N 37/02 | (2006.01) |
| A01N 41/06 | (2006.01) |
| A01N 43/16 | (2006.01) |
| A61Q 5/00 | (2006.01) |
| A61K 8/46 | (2006.01) |
| C09D 5/14 | (2006.01) |
| A61K 8/58 | (2006.01) |
| A61K 8/49 | (2006.01) |
| A61K 8/41 | (2006.01) |
| A61K 8/36 | (2006.01) |
| B27K 3/36 | (2006.01) |
| B27K 1/00 | (2006.01) |
| A01N 55/02 | (2006.01) |
| C09D 4/00 | (2006.01) |

(52) U.S. Cl.
CPC ............ C09D 5/14 (2013.01); A01N 33/00 (2013.01); A01N 37/02 (2013.01); A01N 41/06 (2013.01); A01N 43/16 (2013.01); A01N 43/40 (2013.01); A01N 43/56 (2013.01); A01N 55/02 (2013.01); A61K 8/361 (2013.01); A61K 8/41 (2013.01); A61K 8/466 (2013.01); A61K 8/494 (2013.01); A61K 8/498 (2013.01); A61K 8/4926 (2013.01); A61K 8/58 (2013.01); A61Q 5/006 (2013.01); B27K 1/00 (2013.01); B27K 3/36 (2013.01); C09D 4/00 (2013.01); B27K 2240/20 (2013.01)

(58) Field of Classification Search
None
See application file for complete search history.

(56) References Cited

U.S. PATENT DOCUMENTS

| | | | |
|---|---|---|---|
| 5,009,700 A * | 4/1991 | Rothgery | A01N 43/40 504/126 |
| 5,021,459 A * | 6/1991 | Goettsche | A01N 43/84 514/663 |
| 6,861,395 B2 | 3/2005 | Eastwood et al. | |
| 8,980,792 B2 | 3/2015 | Pearson et al. | |
| 2005/0008576 A1 * | 1/2005 | Makansi | C11D 1/04 424/43 |
| 2011/0092466 A1 | 4/2011 | Groeger et al. | |
| 2012/0004100 A1 | 1/2012 | Hungenberg et al. | |
| 2012/0115722 A1 | 5/2012 | Holyoke, Jr. et al. | |
| 2013/0197276 A1 * | 8/2013 | Spiegler | C07C 43/1785 568/616 |
| 2014/0079806 A1 | 3/2014 | Koop et al. | |
| 2014/0088041 A1 | 3/2014 | Koop et al. | |

FOREIGN PATENT DOCUMENTS

| | | |
|---|---|---|
| AU | 2010/326766 C1 | 6/2011 |
| AU | 2011/206563 A2 | 7/2011 |
| EP | 2366289 A1 | 9/2011 |
| WO | 97/41727 A1 | 11/1997 |
| WO | 01/47487 A1 | 7/2001 |
| WO | 2006/021556 A1 | 3/2006 |
| WO | 2007115766 A1 | 10/2007 |

(Continued)

OTHER PUBLICATIONS

Sigma-Aldrich (http://www.sigmaaldrich.com/catalog/product/sigma/t5535?lang=en&region=US).*

(Continued)

Primary Examiner — Erin E Hirt
(74) Attorney, Agent, or Firm — Lucas & Mercanti, LLP

(57) ABSTRACT

A composition containing succinate dehydrogenase inhibitor and a potentiator has been discovered to enhance the activity of the succinate dehydrogenase such that the amount of the succinate dehydrogenase inhibitor need to effectively treat a microbial substance can be reduced substantially. The compositions may be used as additives for paints and coatings, and protecting crops, seeds, wallboard, metal working fluids, wood from mold, fungi and other microbes.

9 Claims, No Drawings

(56) References Cited

FOREIGN PATENT DOCUMENTS

| WO | 2008/092580 A2 | 8/2008 |
|----|----------------|--------|
| WO | 2009/007233 A2 | 1/2009 |
| WO | 2009/012907 A1 | 1/2009 |
| WO | 2009/098223 A2 | 8/2009 |
| WO | 2010/139653 A1 | 12/2010 |
| WO | 2012/016989 A2 | 2/2012 |
| WO | 2012/052547 A2 | 4/2012 |
| WO | 2012/055673 A1 | 5/2012 |
| WO | 2012/055674 A1 | 5/2012 |
| WO | 2013124275 A1  | 8/2013 |
| WO | 2014/078849 A1 | 5/2014 |

OTHER PUBLICATIONS

Kopfers Performance Chemicals New Zealand, "Statement of Grounds and Particulars. Australia Patent Act 1990—Sections 59, 104(4)," which was submitted in support of the notice of opposition in relation to patent No. 2013344405, dated Jan. 1, 2018, with Australian Patent Office (13 Pages).

* cited by examiner

SUCCINATE DEHYDROGENASE INHIBITOR CONTAINING COMPOSITIONS

CROSS-REFERENCE TO RELATED APPLICATIONS

This application is a Continuation of U.S. patent application Ser. No. 14/442,507 filed May 15, 2015, which is a 371 of PCT/US2013/070777 filed Nov. 19, 2013, which claims the benefit of U.S. Provisional Patent Application No. 61/728,062 filed Nov. 19, 2012. The disclosure of U.S. patent application Ser. No. 14/442,507 is incorporated herein by reference.

FIELD OF THE INVENTION

The present invention relates to a composition of containing a succinate dehydrogenase inhibitor, and uses thereof.

BACKGROUND OF THE INVENTION

The use of succinate dehydrogenase (SDH) inhibitors for controlling phytopathogenic fungi and microorganisms is known from the prior art. For example, U.S. Pat. No. 7,538,073 describes the use of the succinate dehydrogenase (SDH) inhibitor N-[2-(1,3-dimethylbutyl) phenyl]-5-fluoro-1,3-dimethyl-1H-pyrazole-4-carboxamide (referred to below by the common name penflufen) for controlling unwanted microorganisms and phytopathogenic fungi. However, it is known in the art that the use of succinate dehydrogenase inhibitor at low application rates or doses may result in unsatisfactory results.

Combinations of succinate dehydrogenase inhibitors with other active compounds have been suggested in the art. For example, US Patent Application publication 2008/0293566A1 describes the addition of insecticidally active compounds with a carboxamides (which are succinate dehydrogenase inhibitors) to form an active substance combination. The resulting active substance combination has properties for controlling unwanted phytopathogenic fungi and unwanted pests, including animals, insects and acarids.

While the carboxamides have been shown to be effective anti-fungal agents when used in crop protection and have potential for many other material protection and preservative applications, the typical usage of these compounds is in fairly high doses. As a result, many potential uses for these compounds cannot be achieved due to the high cost of the carboxamide compounds. Therefore, there is a need in the art to increase the efficacy of the carboxamide compounds so that they can be used at lower dosages, thereby making the carboxamides more affordable for other potential uses.

Accordingly, there is a need in the art to increase the efficacy of succinate dehydrogenase containing compositions so that these compounds may be used effectively at lower dosages. The present invention provides an answer to that need.

SUMMARY OF THE INVENTION

In one aspect, the present invention provides composition comprising a succinate dehydrogenase inhibitor and an effective amount of a potentiator. It has been discovered that the composition has improved efficacy against microbes, as compared to the inhibitor itself and that the amount of the inhibitor can be reduced to achieve the same level of efficacy.

In another aspect of the present invention, it has been discovered that the composition are also effective as additives for paints and coatings, protecting crops, seeds, wallboard, metal working fluids, wood from fungus and other microbes.

These and other aspects will become apparent when reading the detailed description of the invention.

DETAILED DESCRIPTION OF THE PREFERRED EMBODIMENTS

It has now been surprisingly found certain compounds, called herein "potentiators", can effectively increase the activity of active substances which inhibit succinate dehydrogenase in the mitochondrial respiration chain. As a result, the combination of the succinate dehydrogenase inhibitor with an effective amount of a potentiator has advantages which will be described herein.

In conjunction with the present invention, all active substances which inhibit succinate dehydrogenase in the mitochondrial respiration chain can be used. In a particular embodiment of the present invention, the succinate dehydrogenase inhibitor is a carboxamide compound. Suitable carboxamide compounds include carboxanilides, carboxylic morpholides, benzoic acid amides, and other carboxamides.

Exemplary carboxanilides include, for example, benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxy-carboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyrazole-4-carboxamide and N-(2-(1,3,3-trimethyl-butyl)-phenyl)-1,3-dimethyl-5-fluoro-1H-pyrazole-4-carboxamide.

Exemplary carboxylic morpholides include, for example, dimethomorph, flumorph, and pyrimorph.

Exemplary benzoic acid amides include, for example, flumetover, fluopicolide, fluopyram, and zoxamide.

Exemplary "other" carboxamides include, for example, carpropamid, dicyclomet, mandiproamid, oxytetracyclin, silthiofam, niacinamide, nicotienamide and N-(6-methoxy-pyridin-3-yl) cyclopropanecarboxylic acid amide.

Each of the above carboxamides is known in the art. A few of special mention include the following:

Fluopyram having the chemical name N-{[3-chloro-5-(trifluoromethyl)-2-pyridinyl]-ethyl}-2,6-dichlorobenzamide is a fungicide belonging to the chemical class of pyridylethylbenzamides. Fluopyram, and its manufacturing process starting from known and commercially available compounds, is described in EP-A-1389614.

Penflufen having the chemical name N-[2-(1,3-dimethylbutyl)phenyl]-5-fluoro-1,3-dimethyl-1H-pyrazole-4-carboxamide and its manufacturing process starting from known and commercially available compounds is described in WO 03/010149.

Bixafen having the chemical name N-(3',4'-dichloro-5-fluoro-1,1'-biphenyl-2-yl)-3-(difluoromethyl)-1-methyl-1H-pyrazole-4-carboxamide and its manufacturing process starting from known and commercially available compounds is described in WO 03/070705.

Sedaxane is the mixture of 2 cis-isomers 2'-[(1RS,2RS)-1,1'-bicycloprop-2-yl]-3-(difluoromethyl)-1-methylpyrazole-4-carboxanilide and 2 trans-isomers 2'-[(1RS,2SR)-1,1'-bicycloprop-2-yl]-3-(difluoromethyl)-1-methylpyrazole-4-carboxanilide. Sedaxane and its manufacturing process starting from known and commercially available compounds is described in WO 03/074491, WO 2006/015865 and WO 2006/015866.

Isopyrazam is the mixture of 2 syn-isomers 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 anti-isomers 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide. Isopyrazam and its manufacturing process starting from known and commercially available compounds are described in WO 2004/035589.

Penthiopyrad having the chemical name (RS)—N-[2-(1,3-dimethylbutyl)-3-thienyl]-1-methyl-3-(trifluoromethyl) pyrazole-4-carboxamide and its manufacturing process starting from known and commercially available compounds is described in EP-A-0737682.

Boscalid having the chemical name 2-chloro-N-(4'-chlorobiphenyl-2-yl)nicotinamide and its manufacturing process starting from known and commercially available compounds is described in DE-A 19531813.

Fluxapyraxad having the chemical name 3-(Difluoromethyl)-1-methyl-N-(3',4',5'-trifluorobiphenyl-2-yl)-1H-pyrazole-4-carboxamide and its manufacturing process starting from known and commercially available compounds is described in WO 2006/087343.

In addition to the carboxamide compounds, other succinate dehydrogenase inhibitors include compounds such as 3-nitropropionate and sodium malonate.

The carboxamide compounds may be used as a racemate or in enantiomerically pure form or as an enriched mixture of enantiomers. Also salts or acid addition compounds may also be used. Salts may be sodium, potassium, magnesium, calcium, zinc, aluminum, iron and copper salts of carboxamide. Likewise, it should be understood that the acid addition compounds and in particular adducts with hydrogen halide acids, for example, hydrochloric and hydrobromic acid, carboxylic acids, such as formic acid, acetic acid, tartaric acid and oxalic acid, sulfonic acids, such as p-toluenesulfonic acid and sulfuric acid, phosphoric acid and nitric acid may also be used.

In one particular embodiment of the present invention, the carboxamide is penflufen. Penflufen may be used both as a racemate or in enantiomerically pure form or as an enriched mixture of enantiomers. Also salts or acid addition compounds may also be used. Salts may be sodium, potassium, magnesium, calcium, zinc, aluminum, iron and copper salts of penflufen. Likewise, it should be understood that the acid addition compounds and in particular adducts with hydrogen halide acids, for example, hydrochloric and hydrobromic acid, carboxylic acids, such as formic acid, acetic acid, tartaric acid and oxalic acid, sulfonic acids, such as p-toluenesulfonic acid and sulfuric acid, phosphoric acid and nitric acid may also be used.

The potentiators which may be added to the succinate dehydrogenase inhibitor are generally compounds which exhibit little, if any, antimicrobial properties by themselves, and are generally inexpensive, and readily available compounds within in certain classes of compounds. Classes of potentiators include, chelators, organic acids and esters thereof, amines, amine oxides, ammonium carboxylate salts, aldehydes, efflux pump inhibitors, other enzyme inhibitors, betaines, amides, antioxidants, natural compounds, sulfonamides (respiration inhibitors), and other miscellaneous compounds.

Chelators suitable for use as a potentiator include, for example, iron, calcium, magnesium and other hard metal chelators, as well as chelators for copper or other "soft" metals. Exemplary iron, calcium, magnesium and other hard metal chelators, include, but are not limited to, glycolic acid, salicylic acid, citric acid, 3,4-dihydroxyphenylacetic acid (DOPAC), 4,5-dihydroxy-1,3-benzenedisulfonic acid, diethylenetriaminepentacetic acid (DTPA), N,N'-bis(2-hydroxybenzyl)-ethylenediamine-N,N' diacetic acid (HBED), N,N'-1,2-ethanediylbis-aspartic acid (ethylenediamine disuccinate (EDDS)), 3-hydroxy-2-methyl-4-pyrone (maltol), 1,2-dimethyl-3-hydroxy-4-pyridinone, 8-hydroxyquinoline, phytic acid, N,N-bis(carboxymethyl)-L-glutamic acid (GLDA), salicylaldehyde isonicotinoyl hydrazine (SIH), 1-hydroxyethane 1,1-diphosphonic acid (HEDP), 2-hydroxypyridine-N-oxide, dehydroacetic acid and salts (DHA) and mixtures thereof. Other similar iron, calcium or magnesium chelators may also be used. Suitable copper or other "soft" metal chelators include, but are not limited to, triethylenetetramine, neocuproine, beta-thujaplcin, tropolone, 2,6-pyridinedicarboxlic acid (DPC) and mixtures thereof. Other similar soft metal chelators may also be used.

Organic acids suitable for use as a potentiator include, but are not limited to, for example, lactic acid, tartartic acid, octanoic acid, undecanoic acid, benzoic acid, abietic acid and mixtures or salts thereof. Other similar organic acids may also be used. Esters of organic acids, such as, for example, dodecanoic acid 2,3-diydroxypropyl ester.

Amines suitable for use as a potentiator include, but are not limited to, for example, myristylamine, Tomamine d16 ($C_{16}$ alkyl ether amine), Tomamine d14 ($C_{14}$ alkyl ether amine), N,N-dimethyl-N-decanamine, N,N-dimethyl-N-octylamine, N,N-dimethyl-N-octadecylamine, diisopropanolamine, oleylamine, ethanolamine, ethoxylated amines, such as, N,N',N'-polyoxyethylene(15)-N-tallowalkyl-1,3-diaminopropane, and mixtures thereof. Other similar amines may also be used.

Amine oxides suitable use as a potentiator include trialiphatic substituted amine oxide, N-alkylated cyclic amine oxide, dialkylpiperazine di-N-oxide, alkyldi(hydroxy alkyl) amine oxide, dialkylbenzylamine oxide, fatty amido propyldimethyl amine oxide and diamine oxides or triamine oxides thereof. Other similar amine oxides may also be used.

Ammonium carboxylate salts suitable for use as a potentiator include any ammonium salt of a carboxylic acid. For example, the ammonium cation may be derived from a primary, secondary or tertiary amine precursor used to synthesize any of the above-described carboxamides. Likewise, the carboxylate anion may be the carboxylic acid precursor for one of the above-described carboxamides.

Long chain glycols include, but are not limited to, for example, capryryl glycol, decanediol, and other similar diols.

Amides such as, for example, dodecanamide, may be used.

Betaines such as, for example, cocoamidopropyldimethyl betaine may be used.

Aldehydes suitable for use as potentiators include, but not limited to, for example, cimmamaldehyde, metaldehyde, glutaraldehyde, and mixture thereof. Other similar aldehydes may also be used as the potentiator.

Efflux pump inhibitors (EPI's), include, but are not limited to, for example, phenyl-arginine-b-naphthylamide (PAbN), berberine, reserpine, farnesol, and piperine. Other EFI's may also be used, as well as mixtures thereof.

Other enzyme inhibitors suitable for use as a potentiator, include, but are not limited to, for example, lysozyme.

Suitable natural compounds, include, but are not limited to, for example, thymol, hydroxytyrosol, hydroxychavicol, flavonoids, carvacol, tea tree oil, terpinen-4-ol, allyl isothiocyanate, hexenal, phytoshingosine and other similar compounds. Mixtures of these compounds may also be used.

Suitable sulfonamides (respiration inhibitors), include, but are not limited to, for example, sulfanilamide, p-toluenesulfonamide, 4-carboxbenzenesulfonamide, 4-amino-6-chloro-1,3-benzenedisulfonamide, 4-(2-aminoethyl)benzene sulfonamide, and other similar sulfonamides. Mixture of these sulfonamides may also be used.

Other miscellaneous compounds include, but are not limited to, for example, tetrakis hydroxymethyl phosphonium sulfate, tributyl tetradecyl phosphonium chloride, and guanidine hydrochloride. Other similar compounds may be used as well, as can mixtures of these compounds.

Generally, the succinate dehydrogenase inhibitor is provided with an effective amount of the potentiator in accordance with the invention. An effective amount in this context means any amount of the potentiator that increases the effectiveness of the succinate dehydrogenase inhibitor as compared to the inhibitor alone. For example, the succinate dehydrogenase inhibitor to potentiator mixture is provided in the range of a ratio of about 100:1 to about 1:100 on a weight basis. Typically, the ratio of succinate dehydrogenase inhibitor to potentiator will be in the range of a ratio 50:1 to about 1:50 on a weight basis. More typically the ratio of the components will be in the range of about 10:1 to about 1:10 on a weight basis of the succinate dehydrogenase inhibitor to potentiator. The actual ratios will depend on the potentiator and the particular succinate dehydrogenase inhibitor selected.

In one particular embodiment of the present invention, the potentiator contains a sulfonamide compound. Any of the sulfonamides described above may be used as the potentiator. In an addition embodiment, the sulfonamide is used in conjunction with an additional potentiator.

It has been discovered that the composition of the succinate dehydrogenase inhibitor and the potentiator is more effective against organisms, than the succinate dehydrogenase inhibitor compound alone. Exemplary organisms which the composition has of the present invention are effective against, include, but are not limited to, *Botrytis* spp, *Rhizopus* spp, *Penicillium* spp., *Cladosporium* spp., *Aspergillus* spp, including, for example, *Aspergillus niger*, and *Aspergillus flavus, Alternaria* spp., *Fusarium* spp., Aerobasidium spp., and *Trichoderma* spp.

In addition to the succinate dehydrogenase inhibitor and the potentiator, the composition may further have additional compounds or components which serve as antimicrobial components. These additional compounds or components essentially as co-biocides in the composition. The additional antimicrobial component or composition may be selected based on the activity of the particular component or on the use of the resulting composition.

In the case of wood, such as timber, lumber, and other wood products such as plywood, particle board, fiberboard and oriented strand board (OSB) and wood composites (plastic-wood), the additional compounds or components may be compounds or compositions which are known to have fungicidal, bactericidal or insecticidal properties. In the case of other compositions, such as personal care compositions, for example anti-dandruff shampoos, paints and coating compositions, shampoos, additives to plastics, such as polyvinylchloride and the like, wall board, metal working fluids, crop protection, seed protection, and other similar compositions where mold and fungus may need controlling. Suitable additional components include, for example benzimidazoles, imidazoles, morpholine derivatives, copper compounds, pyrethroids, triazoles, sulfonamides, boron compounds, pyrithione compounds, tertiary amines, haloalkynyl compounds, quaternary ammonium compounds, phenols, pyrroles, strobilurins, phenylsulfamides, zinc compounds and mixtures thereof. Other similar compounds or classes of compounds may be used. Selection of a suitable additional component or co-biocide for a given purpose will be readily apparent to those skilled in the art.

Exemplary benzimidazoles include, but are not limited to, for example, carbendazim, benomyl, fuberidazole, thiabendazole or salts thereof.

Exemplary imidazoles include, but are not limited to, for example, clotrimazole, bifonazole, climbazole, econazole, Fenapanil, irnazalil, isoconazole, ketoconazole, Lombazol, miconazole, Pefurazoat, prochloraz, triflumizole and their metal salts and acid adducts.

Exemplary morpholine derivatives include, but are not limited to, for example, aldimorph, dimethomorph, dodeinorph, falimorph, fenpropidin, fenpropimorph, tridemorph, and Trimorphamid and arylsulfonic acid salts such as p-toluenesulfonic acid and p-dodecylphenyl-sulfonic acid.

Exemplary copper compounds include, but are not limited to, for example, his (N-cyclohexyldiazeniumdioxy)-copper (Cu-HDO), copper (I) oxide, copper (II) oxide, copper carbonate, copper sulfate, copper chloride, copper borate, copper citrate, copper salt of 8-hydroxyquinoline, and copper naphthenate.

Exemplary pyrethroids include, but are not limited to, for example, permethrin, cypermethrin, bifenthrin, cyfluthrin, deltamethrin, prallethrin, fenvalerate, allethrin and etofenprox.

Exemplary triazoles include, but are not limited to, for example, Azaconazole, bitertanol, bromuconazole, cyproconazole, diclobutrazol, difenoconazole, diniconazole, epoxiconazole, etaconazole, fenbuconazole, fluquinconazole, flusilazole, flutriafol, furconazole, hexaconazole, imibenconazole, ipconazole, myclobutanil, metconazole, penconazole, propiconazole, prothioconazole, simeconazole, tehuconazole, tetraconazole, triadimefon, triadimenol, triticonazole and uniconazole and their metal salts and acid adducts.

Exemplary Isothiazolinones include, but are not limited to, for example, N-methylisothiazolin-3-one, 5-chloro-N-methylisothiazolin-3-one, 4,5-dichloro-N-octylisothiazolin-3-one, 5-chloro-N-octylisothiazolinone, N-octyl-isothiazolin-3-one, 4,5-trimethylene-isothiazolinone, 4,5-benzoisothiazolinones, 2n-butyl-1,2-benzisothiazolin-3-one, and 1,2-benzisothiazolin-3-one.

Exemplary sulfonamides include, but are not limited to, for example, dichlofluanid, tolylfluanid, folpet, fluorfolpet, captan and Captofol.

Exemplary boron compounds include, but are not limited to, for example, boric acid, boric acid esters, and borax.

Exemplary pyrithione compounds include, but are not limited to, zinc pyrithione, copper pyrithione, sodium pyrithione and mixtures thereof.

Exemplary tertiary amines include, for example, N-(3-aminopropyl)-N-dodecyl propane-1,3-diamine, N-(3-aminopropyl)-N-decyl-1,3-propanediamine, N-(3-aminopropyl)-N-tetradecyl-1,3-propanediamine as well as their acid addition compounds. Other similar tertiary amines may be used.

Exemplary haloalkynyl compounds include, for example, iodopropynyl carbamates such as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof. Other similar haloalkynyl compounds may also be used.

Phenols which may be used include, for example, tribromophenol, tetrachlorophenol, 3-methyl-4-chlorophenol, 3,5-dimethyl-4-chlorophenol, dichlorophen, 2-benzyl-4-chlorophenol, triclosan, diclosan, hexachlorophene, p-hydroxybenzoic acid, o-phenylphenol, m-Phe-nonylphenol, p-phenylphenol, 4-(2-tert-butyl-4-methyl-phenoxy)-phenol, 4-(2-isopropyl-4-methyl-phenoxy)-phenol,4-(2,4-dimethyl-phenoxy)-phenol and its alkali metal and alkaline earth metal salts. Pentachlorophenol and sodium pentachlorophenolate. Other similar compounds may also be used.

Quaternary ammonium compounds include, for example. Benzalkoniumchloride. Benzyldimethyltetradecylammonium chloride. Benzyldimethyldodecylammonium chloride, Dichlorbenzyldimethylalkylammonium chloride, Didecyldimethylammmonium chloride. Dioctyldimethylammonium chloride, Hexadecyltrimethylammonium chloride, Didecylmethylpoly (oxyethyl), Didecyldimethylammonium carbonate, and Didecyldimethylammonium hydrogen carbonate and ammonium propionate. Polymeric quaternary ammonium compounds, such as Polyhexaethylene Biguanide may also be used. Other quarternary ammonium compounds may also be used.

Pyrrole fungicides such as fludioxinil; strobilurin fungicides such as azoxystrobin; aromatic fungicides such as chlorothalonil; phenylsulfamide fungicides such as, dichlofluanid or tolylfluanid may also be used.

In addition, zinc compounds, such as zinc oxide or zinc borate may also be used.

In addition, compounds and compositions known to have insecticidal properties may be added. Suitable insecticides, include, for example: Abamectin, acephate, acetamiprid, acetoprole, acrinathrin, alanycarb, aldicarb, aldoxycarb, aldrin, allethrin, alpha-cypermethrin. Amidoflumet, amitraz, avermectin, azadirachtin, azinphos A, azinphos M, azocyclotin. *Bacillus thuringiensis*, Barthrin, 4-bromo-2-(4-chloφphenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrifluoron, bromophos A bromophos M, bufencarb, buprofezin, Butathiophos, Butocarboxin, butoxycarboxim. Cadusafos, carbaryl, carbofuran, Carbophenothion, carbosulfan, cartap, chinomethionat. Clo-ethocarb, 4-chloro-2-(2-chloro-2-methylpropyl)-5-[(6-iodo-3-pyridinyl) methoxy]-3(2H)-pyridazinone (CAS RN: 120955-77-3), chlordane, chlorethoxyfos, chlorfenapyr, chlorfenvinphos, chlorfluazuron, chlormephos. N-[(6-Chloro-3-pyridinyl) memyl]-N'-cyano-N-methyl-ethanimid amides Chlopicrin, Chlopyrifos A, chlorpyrifos M, cis-resmethrin, Clocythrin, Clothiazoben. Cypophenothrin clofentezine, coumaphos, Cyanophos, cycloprothrin, cyfluthrin, cyhalothrin, cyhexatin, cypermethrin, cyromazine, decamethrin, deltamethrin, demeton M, demeton S, demeton-S-methyl, diafenthiuron, Dialiphos, diazinon, 1,2-dibenzoyl-1-(1,1-dimethyl)-hydrazine, DNOC, dichlofenthion, dichlorvos, Dicliphos, dicrotophos, Difethialone, diflubenzuron, dimethoate, 3,5-dimethylphenyl methylcarbamate, dimethyl(phenyl)-silyl-methyl-3-phenoxybenzyl ether, dimethyl-(4-ethoxyphenyl)-silylmethyl-3-phenoxybenzyl ether, dimethylvinphos, dioxathion, disulfoton. Eflusilanate, emamectin, empenthrin, endosulfan, o-ethyl-0-(4-nitrophenyl)-1 phenyl phosphonothioat Esfenvalerate, Ethiofencarb, Ethion, etofenprox, Etrimphos, etoxazole, etobenzanid, Fenamiphos, fenazaquin, -oxide, fenfluthrin, fenitrothion, fenobucarb, fenothiocarb, fenoxycarb, fenpropathrin, Fenpyrad, fenpyroximate, fensulfothion, fenthion, fenvalerate, fipronil, flonicamid, fluacrypyrim, fluazuron, flucycloxuron, flucythrinate, Flufenerim, flufenoxuron, Flupyrazofos, Flufenzine, flumethrin flufenprox, fluvalinate, fonophos, Formethanate, formothion, Fosmethilan fosthiazate, Fubfenprox, furathiocarb, Halofenocid, HCH (CAS RN: 58-89-9), heptenophos, hexaflumuron, hexythiazox, hydramethylnon, hydroprene, imidacloprid, imiprothrin, Indoxycarb, Iodfenfos, Iprinomectin, iprobenfos, Isazophos, Isoamidophos, isofenphos, isoprocarb, isoprothiolane, isoxathion, ivermectin, Lama-cyhalothrin, lufenuron, Kadedrin, Lambda-cyhalothrin, lufenuron, malathion, mecarbam, Mervinphos, Mesulfenphos, metaldehyde, metacrifos, methamidophos, methidathion, methiocarb, methomyl, Metalcarb, milbemectin, monocrotophos, Moxiectin, Naled, nicotine, nitenpyram, Noviflumuron, Omethoate, oxamyl, Oxydemethon M, Oxydeprofos, parathion A, parathion M, Penfluron, permethrin, 2-(4-phenoxyphenoxy)-ethyl-ethylcarbamate, Phenthoate, phorate, phosalone, phosmet, phosphamidon, phoxim, pirimicarb, pirimiphos M, pirimiphos A, prallethrin, Profenophos, promecarb, propaphos, propoxur, Prothiophos, prothoate, pymetrozine, Pyrachlophos, pyridaphenthion, Pyresmethrin, pyrethrum, pyridaben, pyridalyl, pyrimidifen, pyriproxyfen, quinalphos pyrithiobac sodium, Resmethrin, rotenone, Salithion, Sebufos, silafluofen, spinosad, spirodiclofen, spiromesifen, sulfotep, sulprofos, Tau-fluvalinate, Taroils, tebufenozide, tebufenpyrad, Tebupirimphos, teflubenzuron, tefluthrin, temephos, Terbam, terbufos, tetrachlorvinphos, tetramethrin, Tetramethacarb, thiacloprid, Thiafenox, thiamethoxam, Thiapronil, thiodicarb, thiofanox, Thiazophos, thiocyclam, Thiomethon, thionazin, thuringiensin, tralomethrin, transfluthrin, Triarathen, triazophos, triazamate, Triazuron, trichlorfon, triflumuron, trimethacarb, Vamidothion, xylylcarb, Zetamethrin;

In addition, Algaecides and herbicides may also be used. Exemplary algaecides and herbicides include, for example: acetochlor, acifluorfen sulfamate, aclonifen, acrolein, alachlor, alloxydim, ametryn, amidosulfuron, Amitrole, ammonium, anilofos, asulam, atrazine, azafenidin, Aziptrotryne, azimsulfuron, Benazolin, benfluralin, benfuresate, bensulfuron, Bensulfide, bentazone, Benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, Carbetamide, carfentrazone-ethyl, Carfenstrole, chlomethoxyfen, chloramben, chlorbromuron, chlrflurenol, chloridazon, chlorimuron, chlornitrofen, Chloroacetic acid, Chloransulam-methyl, cinidon-ethyl, chlorotoluron, chloroxuron, chlorpropham, chlorsulfuron, chlorthal, chlorthiamid, cinmethylin, Cinofulsuron, clefoxydim, clethodim, clomazone, Chlomeprop, clopyralid, cyanamide, cyanazine, Cybutryne, cycloate, cycloxydim, Chloroxynil, clodinafop-propargyl, cumyluron, Clometoxyfen, cyhalofop, cyhalofop butyl, Clopyrasuluron, cyclosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, Dinitramine, dinoseb, dinoseb acetate, dinoterb, diphenamid, dipropetryn, diquat, dithiopyr, diuron, DNOC (2-methyl-4,6-dinitrophenol), DSMA (disodium methylarsenate), (2,4-dichlorophenoxy) acetic acid, daimuron, dalapon, dazomet, 2,4-DB (4-(2,4-dichlphenoxy) butanoic acid), desmedipham, desmetryn, dicamba, dichlobenil, Dimethamid, dithiopyr, dimethametryn, Eglinazine, endothal, EPTC (-Ethyldipropylthiocarbamat) csprocarb, ethalfluralin, Ethidimuron, ethofumesate, Ethobenzanid, ethoxyfen, ethametsulfuron, ethoxysulfuron, Fenoxaprop, fenoxaprop-P, fenuron, flamprop, flamprop-M, flazasulfuron, fluazifop, fluazifop-P, Fuenachlor, fluchloralin, flufenacet flumeturon, flurenol, Fluridone, Fluorocglycofen, Fluoronitrofen, Flupropanate, flurenol, Fluridone, Flurochlorideone, fluroxypyr, fomesafen, Fosamine, Fosametine, flamprop-isopropyl, flamprop-isopropyl-L, flufenpyr, flumiclorac-pentyl, Flumipropyn, Flumioxzim, flurtamone, Flumioxzim, flupyrsulfuron methyl, fluthiacet-methyl, Glyphosate, glufosinate-ammonium, Haloxyfop, hexazinone, imazamethabenz, isoproturon, isoxaben, isoxapyrifop, imazapyr, imazaquin, imazethapyr, ioxynil, isopropalin, imazosulfuron, Imazomox, isoxaflutole, imazapic, Ketospiradox, Lactofen, lenacil, linuron, MCPA (2-(4-chloro-2-methylphenoxy) acetic acid), MCPA-hydrazide, MCPA-thioethyl, MCPB (4-(4-chloro-2-methylphenoxy) butanoic acid), mecoprop, mecoprop-P, mefenacet, Mefluidide, mesosulfuron, metam, metamifop, metamitron, metazachlor, methabenzthiazuron, Methazole, Methoroptryne, Methyldymron, ethylisothiocyanate, metobromuron, metoxuron, metribuzin, metsulfuron, molinate, Monalide, monolinuron, MSMA (monosodium methy arsenate), metolachlor, metosulam, Metobenzuron, naproanilide, napropamide, naptalam, neburon, Nicosulfiiron, norflurazon, sodium chlorate, oxadiazon, oxyfluorfen, Oxysulfuron, orbcncarb, oryzalin, oxadiargyl, Propyzamide, prosulfocarb, pyrazolates, Pyrazolsulfuran, pyrazoxyfen, pyribenzoxim, pyributicarb, pyridate, paraquat, pebulate, pendimethalin, pcntachlorophenol, pentoxazone, Pentanochlor, petroleum oils, phenmedipham, picloram, piperophos, pretilachlor, primisulfuron, Prodi amines profoxydim, prometryn, propachlor, propanil, Propaquizafob, Propazine, propham, Propisochlor, pyriminobacmethyl, pelargonic pyrithiobac, pyraflufen-ethyl, Quinmerac, Quinocloamine, quizalofop, quizalofop-P, quinchlorac, Rimsulfuron sethoxydim, Sifuron, Simazine, simetryn, sulfosulfuron, sulfometuron, sulfentrazone, sulcotrione, sulfosate, Creosote TCA (trichloroacetic acid), TCA-sodium, tebutam, tebuthiuron, terbacil, terbumeton, Terbuthylazine, terbutryn, Thiazafluoron, thifensulfuron, thiobencarb, thiocarbazil, tralkoxydim, triallate, triasulfuron, tribenuron, triclopyr, tridiphane, Trietazine, trifluralin, TYCOR, thidiazimin, thiazopyr, triflusulfuron, Vernolate.

The composition containing the succinate dehydrogenase inhibitor of the present invention may be used in the customary formulations, such as solutions, emulsions, suspensions, powders, foams, pastes, granules, aerosols and very fine capsules in polymeric substances. It is also possible to encapsulate the succinate dehydrogenase inhibitor and/or additional biocide.

In addition, by mixing the active compounds with extenders, such as liquid solvents, liquefied gases under pressure and/or solid carriers, and optionally with the use of surfactants, emulsifiers and/or dispersants, the composition may be applied to a surface or article in need of treatment. Suitable solvents include, water, organic solvents such as, for example, xylene, toluene or alkyl naphthalenes, chlorinated aromatics or chlorinated aliphatic hydrocarbons, such as chlorobenzenes, chloride or methylene chloride, aliphatic hydrocarbons such as cyclohexane or paraffins, for example petroleum fractions, alcohols, such as butanol, glycerol, and ethers and esters, ketones, such as acetone, methyl ethyl ketone, methyl isobutyl ketone or cyclohexanone, strongly polar solvents such as dimethylformamide and dimethylsulphoxide, as well as water. Liquefied gaseous extenders or carriers are meant liquids which are gaseous at normal temperature and under normal pressure, for example aerosol propellants, such as halogenated hydrocarbons as well as butane, propane, nitrogen and carbon dioxide. Suitable solid carriers are: for example ground natural minerals, such as kaolins, clays, talc, chalk, quartz, attapulgite, montmorillonite or diatomaceous earth, and ground synthetic minerals, such as highly disperse silica, alumina and silicates. As solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks. As emulsifying and/or foam formers are: for example nonionic and anionic emulsifiers, such as polyoxyethylene fatty acid esters, polyoxyethylene fatty alcohol ethers, for example alkylaryl, alkyl sulfates, aryl sulphonates as well as albumin. Suitable dispersants are: for example ligninsulfite was liquors and methylcellulose.

The present invention is further described in detail by means of the following Examples. The following examples are meant to show the effects of potentiator with succinate dehydrogenase inhibitor and are not intended to be limiting.

EXAMPLES

Example 1

Sample stock solution of Penflufen was prepared in DMSO at 20000 ppm (active ingredient). Serial dilutions of Penflufen and the potentiators were made in DMSO in a 96 well plate and 10 ul of solution from each well was transferred into a new flat bottom 96 well plate to run a microtiter plate minimum inhibitory concentration (MIC) test. The potentiators tested are shown in Table 1.

TABLE 1

| Potentiators | |
| --- | --- |
| Potentiator | Chemical name/composition |
| Ethoduomeen | Tris(2-hydroxyethyl)-N-tallowalkyl-1,3-diaminopropane |
| Barlene 12 | N,N-Dimethyl-N-dodecylamine |
| HPNO | 2-hydroxypyridine-N-oxide |
| Barlox 12 | cocoamine oxide |
| Isononoic Acid | — |
| Oleylamine | (Z)-Octa-9-decenylamine |
| Toluene sulfonamide | — |
| DHA Zn | Dehydroacetic acid zinc salt |

Microorganisms grown on agar slants were harvested using standard microbiological techniques. The numbers of mold spores were determined by counted using a hemocytometer, and then inoculum was prepared in the media shown in Table 2. Then, 190 ul of inoculum was added into each well containing 10 ul of the serially diluted sample solution. The start-up concentration of the sample was 1000 ppm containing 5% of DMSO. The final concentration of mold spores were set up at approx. $10^4$/mL.

Table 2 shows the details on test organisms, suitable culture broth and incubation conditions. After the incubation, data were collected: the lowest concentrations that visually inhibited the microbial growth were recorded as the MICs (Tables 3A, 3B, 3C, 3D and 3E).

TABLE 2

List of microorganisms tested, culture media and incubation condition.

| Microorganism (source) | incubation | Incubation condition | media |
|---|---|---|---|
| Aspergillus brasiliensis (ATCC 16404) (TABLE 3A) | 28° C.-7 days | Aerobically | Sucrose 20.0 g/liter Sodium Nitrate 2.0 g |
| Aureobasidium pullulans (ATCC 9348) (TABLE 3B) | 28° C.-7 days | Aerobically | Dipotassium Phosphate 1.0 g Magnesium Sulfate 0.5 g |
| Aspergillus niger (ATCC 9642) (TABLE 3C) | 28° C.-7 days | Aerobically | Potassium Chloride 0.5 g Yeast extract 0.1 g |
| Trichoderma virens (ATCC 9645) (TABLE 3D) | 28° C.-7 days | Aerobically | Ferrous Sulfate 0.01 g |
| Penicillium funiculosum (ATCC 11797) (TABLE 3E) | 28° C.-7 days | Aerobically | |

TABLE 3A

| A. brasiliensis | MIC alone | MIC combination | |
|---|---|---|---|
| | | Potentiator | Penflufen |
| Penflufen | 15.65 | | |
| Ethoduomeen | <4.88 | 4.88 | 0.97 |
| Barlene 12 | 31.25 | 7.81 | 7.81 |
| HPNO | 1250 | 156.25 | 31.5 |
| Barlox 12 | 62.5 | 3.9 | 7.81 |
| Isononoic acid | 1250 | 78.12 | 15.62 |
| Oleylamine | 2.5 | 0.625 | 15.62 |
| Toluene sulfonamide | 5000 | 39 | 7.81 |
| DHA Zn | 500 | 62.5 | 62.5 |

TABLE 3B

| A. pullulans | MIC alone | MIC combination | |
|---|---|---|---|
| | | Potentiator | Penflufen |
| Penflufen | 500 | | |
| Ethoduomeen | 9.76 | <2.44 | <0.488 |
| Barlene 12 | 7.81 | 3.9 | 3.9 |
| HPNO | 1250 | 312.5 | 62.5 |
| Barlox 12 | 15.62 | 7.81 | 15.62 |
| Isononoic acid | 625 | 625 | 125 |
| Oleylamine | 0.31 | 0.31 | 7.81 |
| Toluene sulfonamide | 5000 | 625 | 125 |
| DHA Zn | 1000 | 62.5 | 62.5 |

TABLE 3C

| T. virens | MIC alone | MIC combination | |
|---|---|---|---|
| | | Potentiator | Penflufen |
| Penflufen | >1000 | | |
| Ethoduomeen | <4.88 | 4.88 | 0.97 |
| Barlene 12 | 7.81 | 15.65 | 15.62 |
| HPNO | 1250 | 625 | 125 |
| Barlox 12 | 125 | 15.62 | 31.25 |
| Isononoic acid | 625 | 625 | 125 |
| Oleylamine | 0.625 | 1.25 | 31.25 |
| Toluene sulfonamide | 5000 | 1250 | 250 |
| DHA Zn | 250 | >500 | >500 |

TABLE 3D

| A. niger | MIC alone | MIC combination | |
|---|---|---|---|
| | | Potentiator | Penflufen |
| Penflufen | 7.81 | | |
| Ethoduomeen | <4.88 | 4.88 | 0.97 |
| Barlene 12 | 250 | 15.62 | 15.62 |
| HPNO | 625 | 39 | 7.81 |
| Barlox 12 | 15.62 | 7.81 | 15.62 |
| Isononoic acid | 625 | 39 | 7.81 |
| Oleylamine | 1.25 | 0.31 | 7.81 |
| Toluene sulfonamide | 5000 | 19.5 | 3.9 |
| DHA Zn | 500 | NA | NA |

TABLE 3E

| P. pinophilum | MIC alone | MIC combination | |
|---|---|---|---|
| | | Potentiator | Penflufen |
| Penflufen | >1000 | | |
| Ethoduomeen | <4.88 | 4.88 | 1.95 |
| Barlene 12 | 7.81 | 15.62 | 15.65 |
| HPNO | 1250 | 625 | 125 |
| Barlox 12 | 62.5 | 15.62 | 61.25 |
| Isononoic acid | 625 | 625 | 125 |
| Oleylamine | 1.25 | 0.31 | 7.81 |
| Toluene sulfonamide | 5000 | 625 | 125 |
| DHA Zn | >1000 | >500 | >500 |

As can be seen from the above tables, each of the listed potentiators reduces the amount of the active ingredient Penflufen. Against certain microbial agents, the combination of the potentiator and the active can achieve a 1-fold, 2-fold or more reduction in that amount of the active ingredient needed to inhibit growth of the microbial agent.

Example 2

Total 17 samples, including Penflufen, 8 Penflufen-potentiator blends and 8 potentiators were submitted for evaluation. The concentrations of Penflufen and potentiators in the samples are shown in Table 4.

TABLE 4

| Sample Name | Ratio of Pot./Act. | Active Conc. (ppm) | Potentiator conc. (ppm) |
|---|---|---|---|
| Penflufen blend with Barlene 12 | 1x | 10,000 | 10,000 |
| Penflufen blend with Barlox 12 | 0.5x | 10,000 | 5,000 |
| Penflufen blend with Ethoduomeen | 5x | 10,000 | 50,000 |
| Penflufen blend with Sodium benzoate | 5x | 10,000 | 50,000 |
| Penflufen blend with Oleylamine | 0.1x | 10,000 | 1,000 |
| Penflufen blend with HPNO | 5x | 10,000 | 50,000 |
| Penflufen blend with Isononoic Acid | 5x | 10,000 | 50,000 |
| Penflufen blend with DHA-Zn | 1x | 10,000 | 10,000 |
| Barlene 12 | | | 10,000 |
| Barlox 12 | | | 5,000 |

TABLE 4-continued

| Sample Name | Ratio of Pot./Act. | Active Conc. (ppm) | Potentiator conc. (ppm) |
|---|---|---|---|
| Ethoduomeen | | | 50,000 |
| Sodium benzoate | | | 50,000 |
| Oleylamine | | | 1,000 |
| HPNO | | | 50,000 |
| Isononoic Acid | | | 50,000 |
| DHA-Zn | | | 10,000 |
| Penflufen | | 10,000 | |

Procedure

Decay fungi *Antrodia sinuosa* and *Coniophora puteana* were obtained from GTS microbiology lab fungal collection and cultured on Potato Dextrose Agar at 28° C.

The samples were diluted to test at a starting concentration of 1,000 ppm active based on the concentration of Penflufen in the samples. Samples were serially diluted into the molten Potato Dextrose Agar before the agar was solidified. The agar plugs with active fungal hyphae growth were inoculated onto the prepared agar surface. The agar plates were incubated at 28° C. for 9 days and following incubation, the minimum concentration of active observed to completely inhibit hyphae growth (MIC) was determined with stereo microscopic verification.

Results

Table 5 shows the MIC values of Penflufen, potentiators and potentiation blends against decay fungi.

All concentrations reported are in ppm. "Active" indicates Penflufen present; "Potentiator" is the potentiator in each sample. "Act" and "Pot" are the concentrations of active and potentiator respectively at the highest dilution to inhibit growth (MIC value). The initial row highlighted in red with only a value for active is the MIC for the active alone; each row with only a value for potentiator is the MIC for that potentiator alone. Any combination in which the MIC value was reduced by greater than 75% (2 levels of 2× dilution) of the MIC of the active alone is highlighted in green.

Comments

There are eight out of nine Penflufen-potentiator blends tested for this study showed evidence of potentiation against two decay fungi with significant MIC reductions ranging from 75% up to 94% compared to the Penflufen alone.

Table 5

TABLE 5

The MIC values of Penflufen, potentiators and potentiation blends against decay fungi.

| Active | Potentiator | Pot./Act. Ratio | *Antrodia sinuosa* MIC (ppm) Act. | *Antrodia sinuosa* MIC (ppm) Pot. | *Coniophora puteana* MIC (ppm) Act. | *Coniophora puteana* MIC (ppm) Pot. |
|---|---|---|---|---|---|---|
| Penflufen | | | 62.5 | | 125 | |
| | Barlene 12 | | | 250 | | 500 |
| Penflufen | Barlene 12 | 1x | 7.8 | 7.8 | 31.3 | 31.3 |
| | Barlox 12 | | | 62.5 | | 250 |
| Penflufen | Barlox 12 | 0.5x | 7.8 | 3.9 | 31.3 | 15.6 |
| | Ethoduomeen | | | 625 | | 2500 |
| Penflufen | Ethoduomeen | 5x | 3.9 | 19.5 | 31.3 | 156 |
| | Sodium benzoate | | | 1250 | | 313 |
| Penflufen | Sodium benzoate | 5x | 15.6 | 78.1 | 15.6 | 78.1 |
| | Oleylamine | | | 50.0 | | 50.0 |
| Penflufen | Oleylamine | 0.1x | 15.6 | 1.6 | 31.3 | 3.1 |
| | HPNO | | | 313 | | 313 |
| Penflufen | HPNO | 5x | 15.6 | 78.1 | 31.3 | 156 |
| | Isononoic acid | | | 313 | | 156 |
| Penflufen | Isononoic acid | 5x | 15.6 | 78.1 | 15.6 | 78.1 |
| | DHA-Zinc | | | 125 | | 125 |
| Penflufen | DHA-Zinc | 1x | 15.6 | 15.6 | 15.6 | 15.6 |

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. An anti-microbial composition comprising:
   a succinate dehydrogenase inhibitor; and
   a potentiating amount of a potentiator to increase anti-microbial efficacy of the succinate dehydrogenase inhibitor;
   wherein the succinate dehydrogenase inhibitor is penflufen;
   wherein the potentiator is selected from the group consisting of N,N-dimethyl-N-dodecylamine, cocoamine oxide, oleylamine and mixtures thereof;
   wherein the weight ratio of the succinate dehydrogenase inhibitor to potentiator is about 10:1 to about 1:1; and
   wherein the potentiating amount is an amount of the potentiator that allows a reduction in the amount of penflufen in the combination while providing anti-microbial efficacy equivalent to or greater than a composition containing penflufen alone.

2. The composition according to claim 1, further comprising an additional antimicrobial component.

3. The composition according to claim 2, wherein the additional antimicrobial component is selected from the group consisting of benzimidazoles, imidazoles, morpholine derivatives, copper compounds, pyrethroids, triazoles, sulfonamides, boron compounds, pyrithione compounds and mixtures thereof.

4. The composition according to claim 3, wherein the additional antimicrobial component comprises zinc pyrithione.

5. A method of treating wood comprising applying a composition according to claim 1 to wood.

6. The treated wood prepared in accordance with the method according to claim 5.

7. The composition according to claim 1, wherein the potentiator is N,N-dimethyl-N-dodecylamine.

8. The composition according to claim 1, wherein the potentiator is cocoamine oxide.

9. The composition according to claim 1, wherein the potentiator is oleylamine.

* * * * *